United States Patent
Opahle et al.

(10) Patent No.: US 7,083,583 B2
(45) Date of Patent: Aug. 1, 2006

(54) ORTHESIS COMPRISING AN ADJUSTABLE RANGE OF MOVEMENT

(75) Inventors: Hans-Georg Opahle, Rosenheim (DE); Erich Albrecht, Neubeuern (DE)

(73) Assignee: Albrecht GmbH (DE)

( * ) Notice: Subject to any disclaimer, the term of this patent is extended or adjusted under 35 U.S.C. 154(b) by 0 days.

(21) Appl. No.: 10/505,359

(22) PCT Filed: Feb. 20, 2003

(86) PCT No.: PCT/EP03/01752

§ 371 (c)(1),
(2), (4) Date: Aug. 19, 2004

(87) PCT Pub. No.: WO03/070129

PCT Pub. Date: Aug. 28, 2003

(65) Prior Publication Data

US 2005/0215931 A1   Sep. 29, 2005

(30) Foreign Application Priority Data

Feb. 22, 2002 (DE) .............................. 102 07 702

(51) Int. Cl.
*A61F 5/00* (2006.01)

(52) U.S. Cl. ........................... 602/16; 602/23; 602/62; 602/5

(58) Field of Classification Search .................. 602/16, 602/5, 20, 23, 26, 27, 12, 62, 63, 24, 25
See application file for complete search history.

(56) References Cited

U.S. PATENT DOCUMENTS

| 5,873,847 A | 2/1999 | Bennett et al. |
| 6,203,511 B1 | 3/2001 | Johnson et al. |

*Primary Examiner*—Henry Bennett
*Assistant Examiner*—Camtu Nguyen
(74) *Attorney, Agent, or Firm*—Myers & Kaplan, LLC; Sandra M. Drummond; Joel D. Myers

(57) ABSTRACT

The invention relates to an orthesis comprising a first bar (2) and a second bar (3) joined to the latter in an articulated manner, in addition to at least one click-stop dial (14, 15), for adjusting the pivoting-range stops in an extensional or flexional direction. The invention is also provided with a fixing device, which comprises a locking disc (16) that is mounted in a rotationally fixed manner in relation to the first bar (2) and can be displaced in the direction of the pivoting axis (102), for blocking the click-stop dial (14, 15). The locking disc (16) can be moved by being displaced between a position that blocks the click-stop dial (14, 15) by radial impingement, in which the locking disc (16) engages with the click-stop dial (14, 15) in a locking positive fit and a release position, in which the locking disc (16) is disengaged from said click-stop dial (14, 15).

10 Claims, 7 Drawing Sheets

Figure 1:
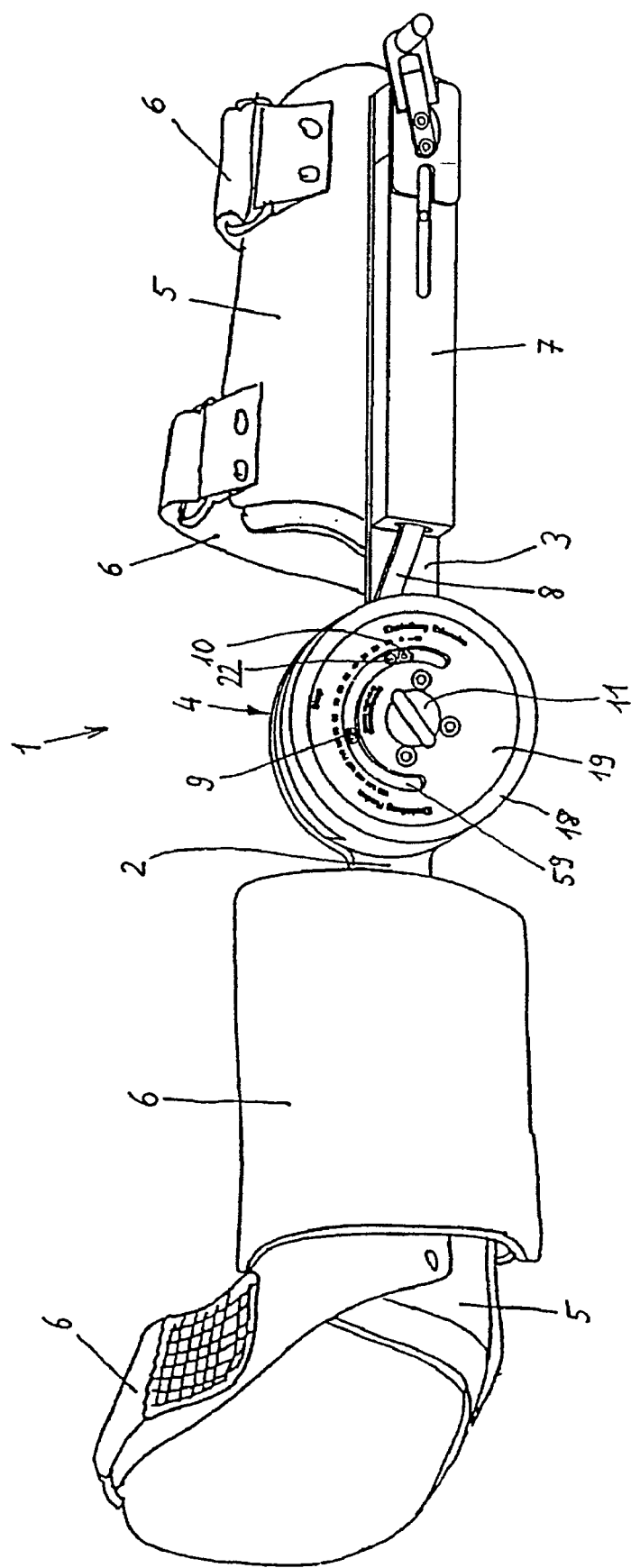

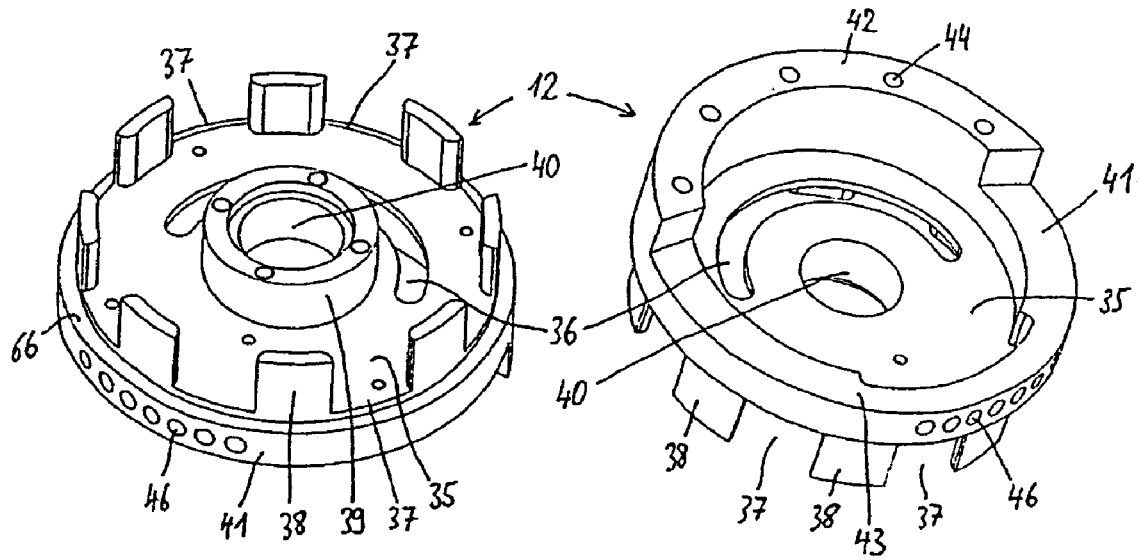
Fig. 4A
Fig. 4B
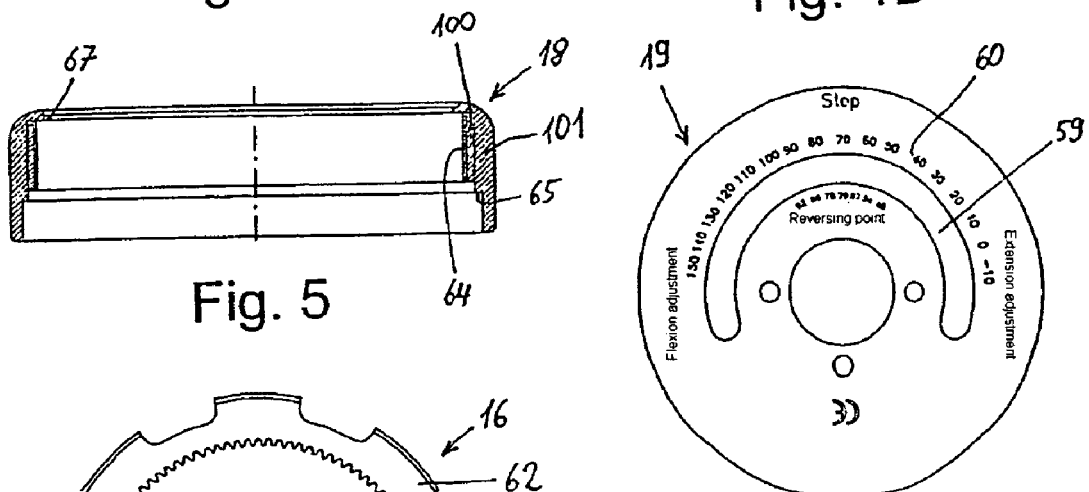
Fig. 5
Fig. 6
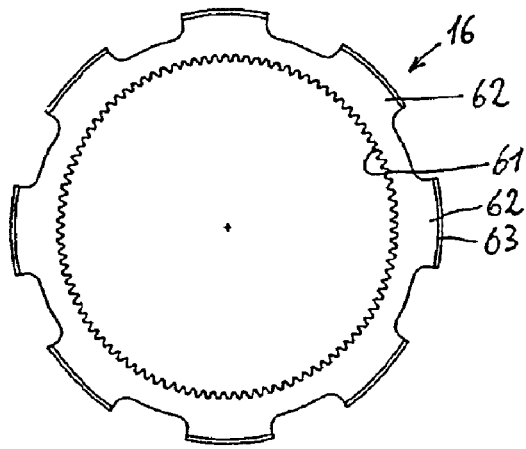
Fig. 7A
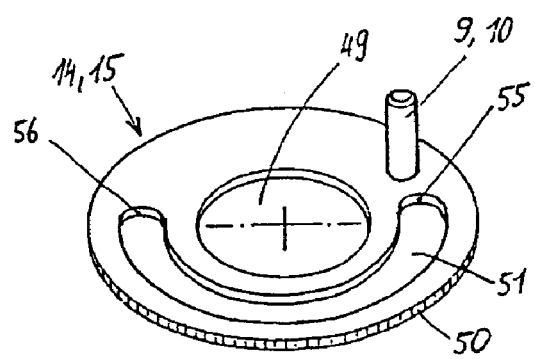
Fig. 8
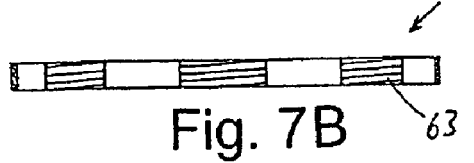
Fig. 7B

ORTHESIS COMPRISING AN ADJUSTABLE RANGE OF MOVEMENT

The invention relates to an orthesis, for example an elbow orthesis, particularly for reduction of extension and/or flexion deficits, in accordance with the preamble of claim 1.

Joint capsules and/or connective tissue, in particular, often have an extension deficit and/or flexion deficit after, for example, ligament operations, accidents, inflammation, etc. This means that a distal body part, for example a forearm, can no longer be brought completely to its normal extension or flexion position in relation to a proximal body part, for example an upper arm.

As is known, ortheses are used to guide such joints, particularly during movement. Moreover, the orthesis is intended to limit the movement of the joint in the extension and/or flexion direction in such a way that injuries caused by excessive strain are ruled out.

Moreover, in order to stretch out the contractions and shrinkages in the area of the joint, use is also made of what are referred to as quengel devices, i.e. ortheses which are pretensioned by a spring and which support the movement of the body part as far as the desired extension or flexion limit.

In ortheses, the extension and flexion limit stop must be able to be adjusted within wide limits in order to satisfy the individual requirements of the patient. Moreover, it is desirable to permit straightforward and rapid adjustability of the pivot range limits so that, with increasing mobilization of the joint, the pivot range limits can be suitably readjusted with ease and speed.

To limit the pivot range, known ortheses used for stretching have limit stop pins which can be inserted into different bores arranged around the pivot axis. A disadvantage of these, however, is that adjustment of the extension and flexion limit stop is possible only in fairly large increments, for example in 15° increments, and the pivot range limits for this reason often cannot be adjusted with sufficient precision.

U.S. Pat. No. 5,873,847 discloses an orthesis in which there are no insertable limit stop pins, but instead two click-stop dials arranged one behind the other for adjusting the pivot range limits in the extension direction and flexion direction. To block these click-stop dials, a fixing device is provided in the form of two pressure plates which can be clamped together by means of a screw and in this way clamp the click-stop dials lying between them. A disadvantage of this, however, is that in order to adjust the pivot range limits, a tool is needed for releasing the fixing device and then for clamping it together again. Such a tool is often not immediately to hand when needed. Another problem is that the click-stop dials have to be clamped together relatively firmly in order to rule out the possibility of undesired rotation of the limit stops. This requires that a certain force be applied when tightening and releasing the fixing device. If the fixing screw is not sufficiently tightened, this can lead to undesired rotation of the click-stop dials and thus to an overextension of the muscles, ligaments or tendons.

Therefore, it is an object of the invention to make available an orthesis of the type mentioned at the outset, with which the flexion and/or extension limit stop can be adjusted and blocked in a straightforward, rapid, precise and reliable way.

According to the invention, this object is achieved by the features of claim 1. Advantageous embodiments of the invention are described in the further claims.

In the orthesis according to the invention, the fixing device has a locking disk which is displaceable in the direction of the pivot axis and is mounted in a rotationally fixed manner in relation to the first bar. This locking disk can be moved, by being displaced, between a blocking position, in which the locking disk engages radially over the click-stop dial and is in locked form-fit engagement with said click-stop dial, and a release position, in which the locking disk is disengaged from the click-stop dial.

Thus, in the orthesis according to the invention, the locking of the at least one click-stop dial is effected by means of an axially displaceable locking disk which, in the engagement position, is in form-fit engagement with the click-stop dial and, in the release position, is no longer in contact with the click-stop dial. Axially displaceable in this context means that the locking disk is displaceable in the direction of its own axis of rotation and thus in the direction of the pivot axis of the bar hinge.

By virtue of the fact that the rotationally fixed locking disk is no longer in engagement with the click-stop dial via a force fit, but instead via a form fit, undesired rotation of the click-stop dial is excluded. The form-fit connection is expediently obtained by means of the click-stop dial having an outer toothing, and the locking disk having an inner toothing which can be moved into and out of meshing engagement with the outer toothing of the click-stop dial.

The displacement of the locking disk in the axial direction is expediently effected by means of a rotation part, for example a rotatable cover part, which has an internal thread and is in engagement with an external thread of the locking disk. When the rotation part is moved, the locking disk moves in the manner of a spindle in the axial direction and can thus be brought into and out of engagement with the click-stop dial. When the locking disk is disengaged from the click-stop dial, said click-stop dial can be brought to the desired rotation position until the associated pivot range stop is in the desired angle position. Moreover, by turning the rotation part in the opposite direction, the locking disk is brought back into engagement with the click-stop dial and thus blocks the latter.

The extension and/or flexion limit stop can thus be adjusted and blocked in a very straightforward, rapid, precise and reliable way, and without using a tool.

Figure 2:
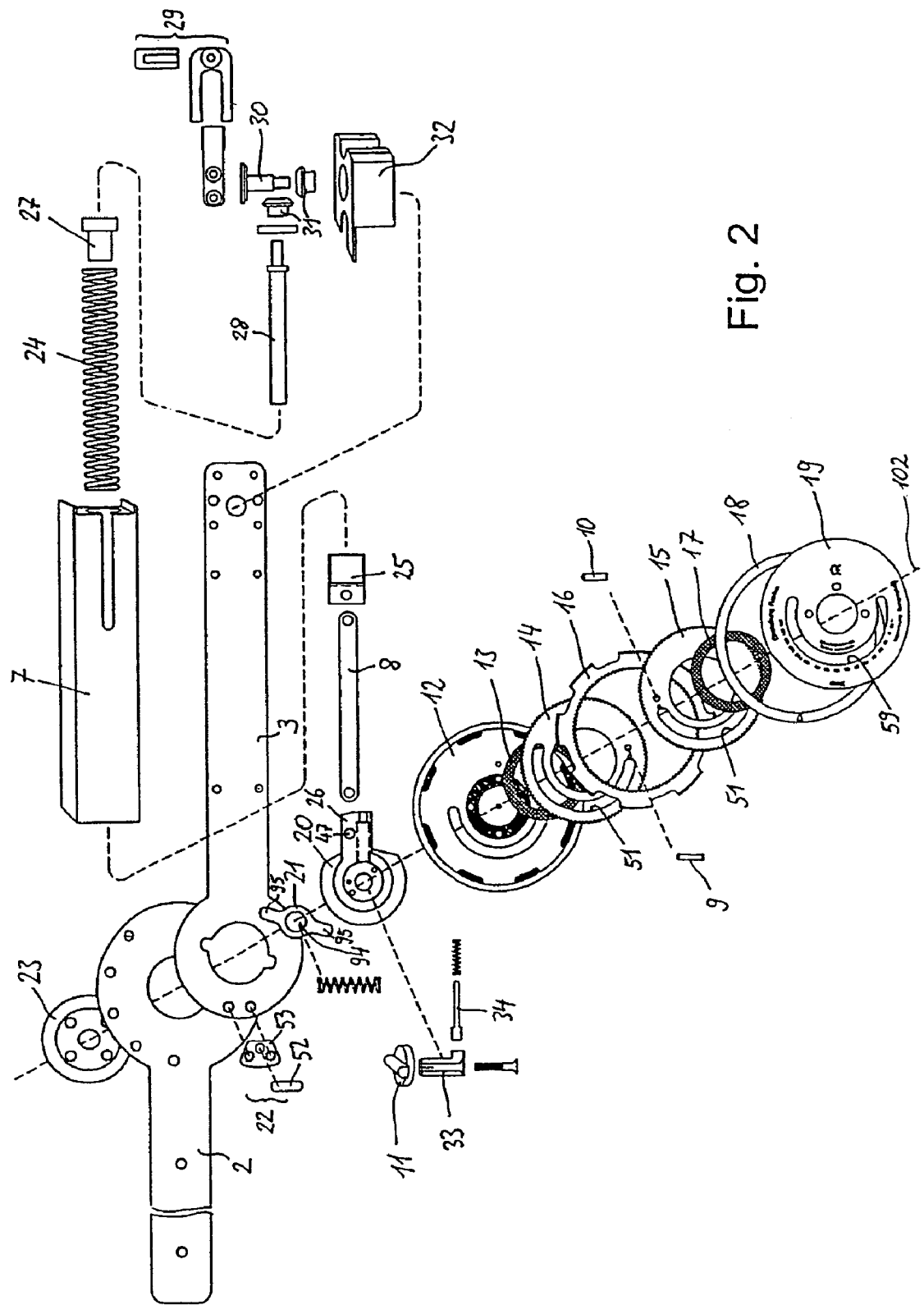
Figure 3:
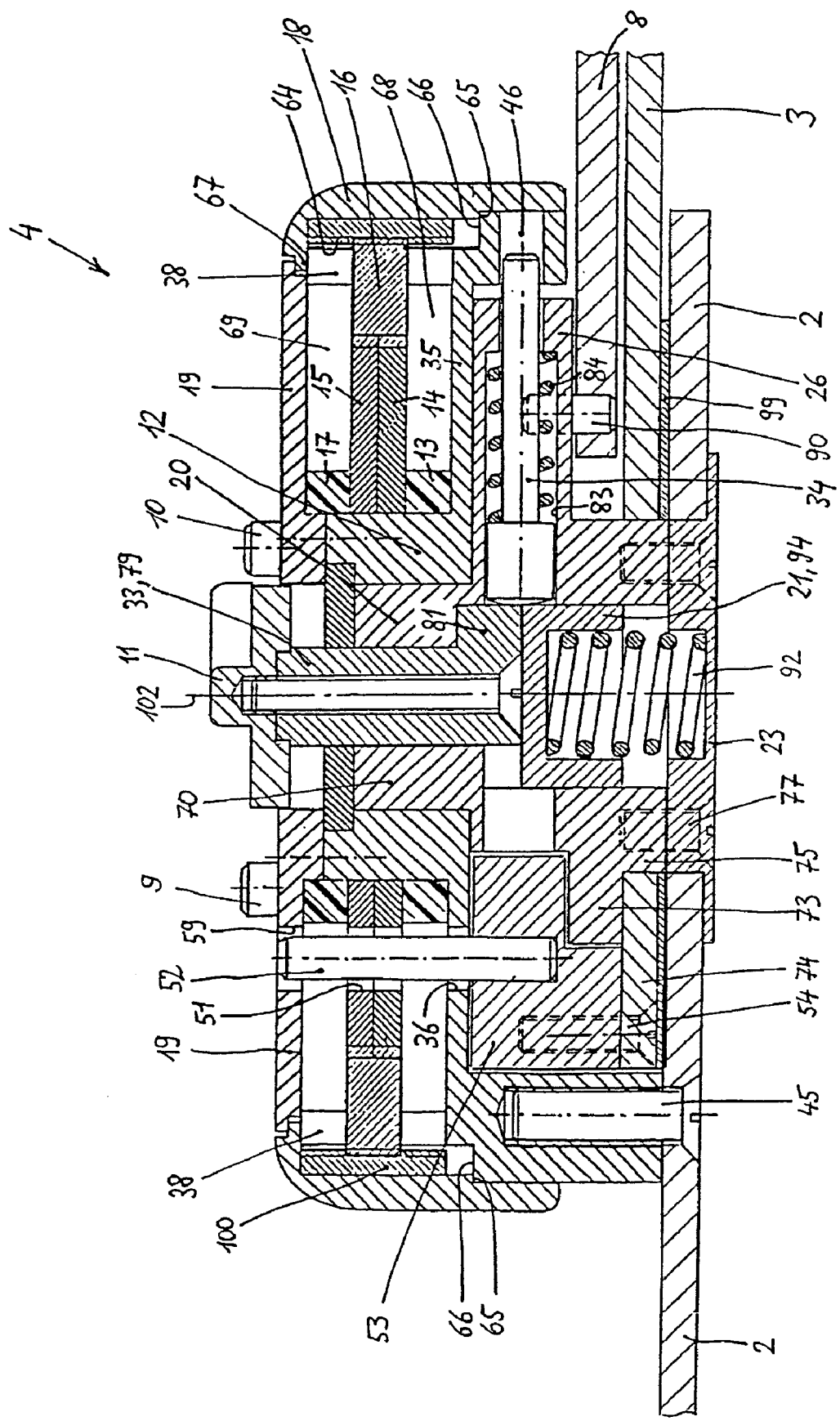
Figure 9:
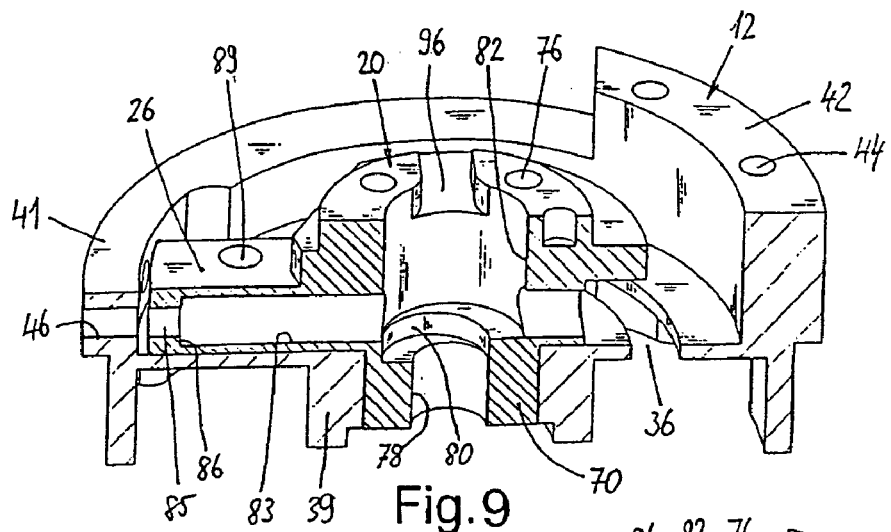
Figure 10:
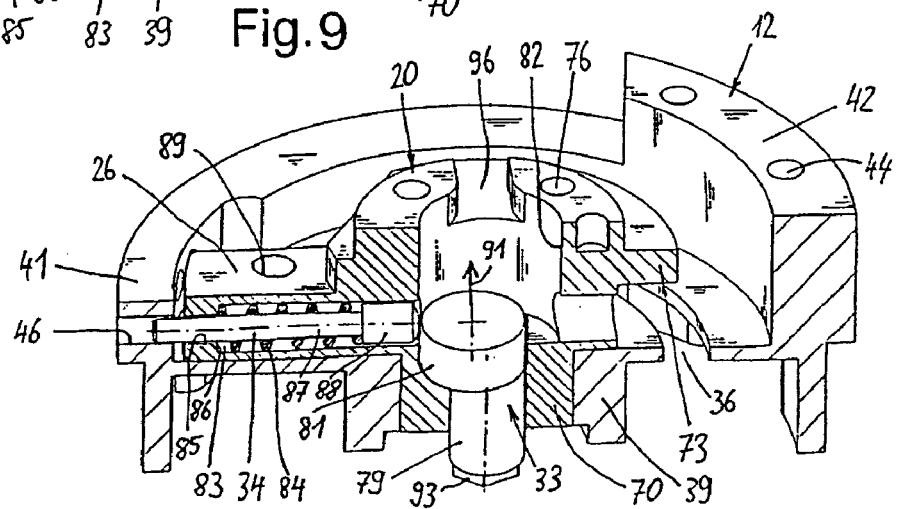
Figure 11:
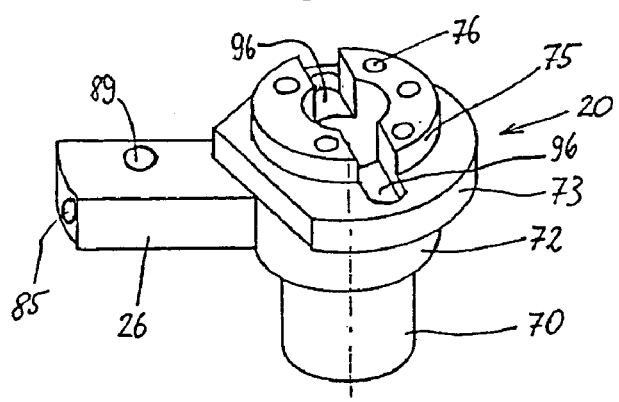
Figure 12A:
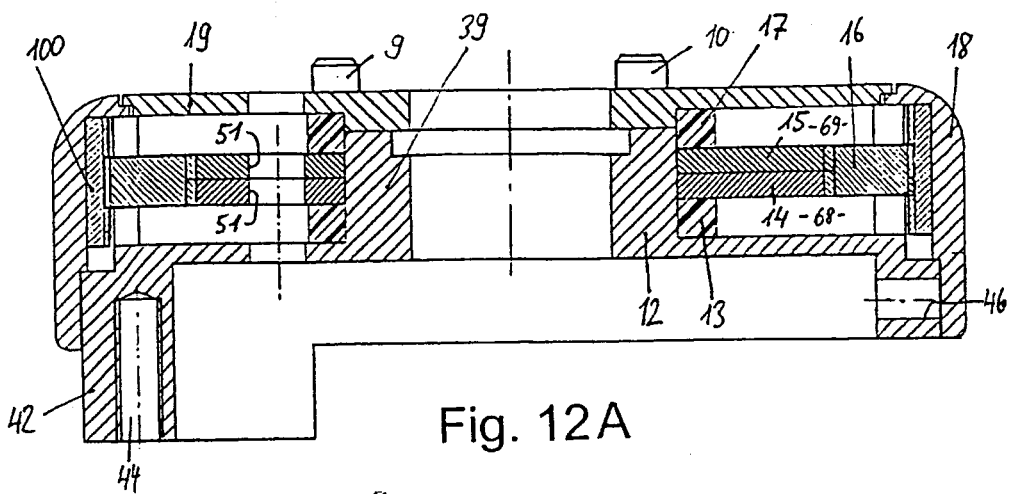
Figure 12B:
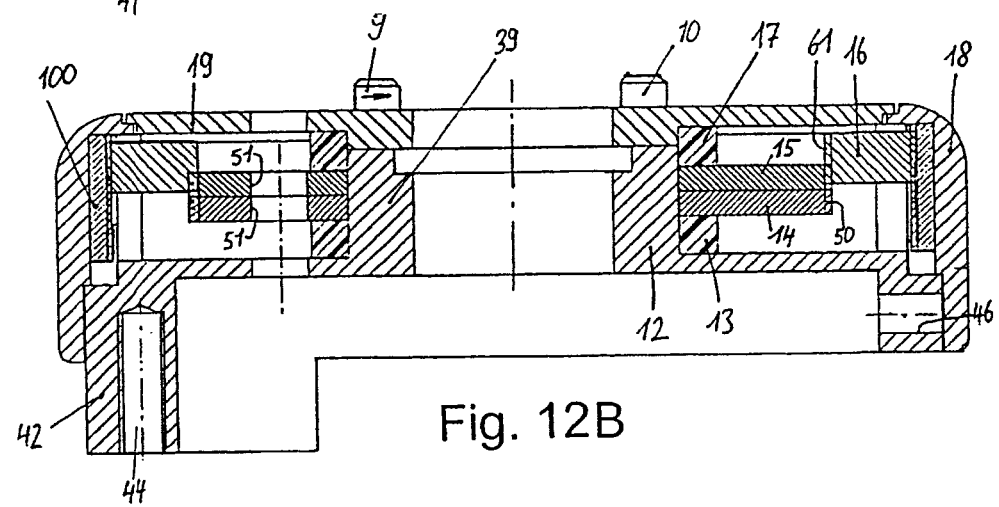
Figure 12C:
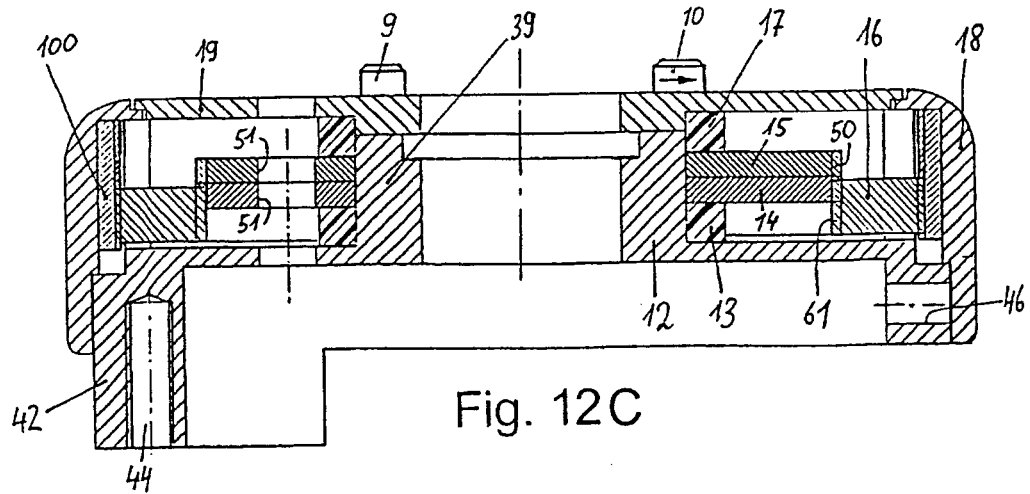
Figure 13:
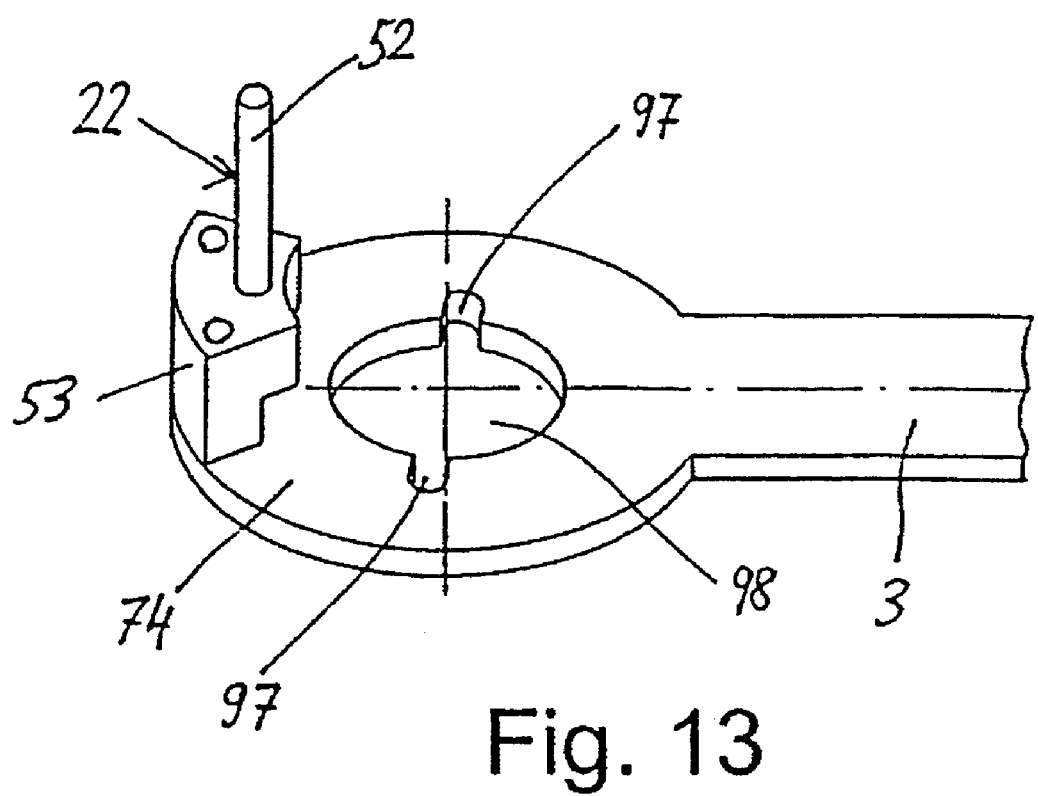

An example of the invention is explained in more detail below with reference to the drawings, in which:

FIG. 1 shows a perspective view of the orthesis according to the invention,

FIG. 2 shows an exploded view of the individual parts of the orthesis from FIG. 1, FIG. 3 shows a longitudinal section through the bar hinge of the orthesis from FIG. 1, FIGS. 4A and 4B show an oblique view of a housing from above and from below, respectively, FIG. 5 shows a longitudinal section through a rotation part, FIG. 6 shows a plan view of a cover plate, FIGS. 7A and 7B show a plan view and side view, respectively, of a locking disk, FIG. 8 shows a perspective view of a click-stop dial, FIG. 9 shows a longitudinal section through the housing, with inserted rotation block of a dead-point adjustment mechanism, FIG. 10 shows a view according to FIG. 9, also with insertion of a blocking pin with compression spring and an eccentric part, FIG. 11 shows a perspective view of the rotation block, FIGS. 12A to 12C show a longitudinal section through the housing with two click-stop dials and the fixing device for blocking the click-stop dials, with the locking disk situated in the locking position and in two different release positions, and FIG. 13 shows a perspective view of a portion of the second bar with fitted limit stop element.

FIG. 1 depicts an orthesis 1 for reducing extension and/or flexion deficits of elbow joints, with a first bar 2 to be fastened to the upper arm, and with a second bar 3 which is to be fastened to the forearm and which is connected to the first bar 2 in an articulated manner via a bar hinge 4. They are fastened to the upper arm and forearm, respectively, in a known manner by means of half-shells 5, which are arranged on the first bar 2 and second bar 3, and via tapes or straps 6 which are wound round the upper arm and forearm.

The orthesis shown is designed to be applied only on one side of the joint in question. However, it is also conceivable for a joint to be provided with two such ortheses, which are then applied on different sides of the joint.

Moreover, the orthesis shown has a spring force mechanism with a spring housing 7, in which a compression spring (not visible in FIG. 1) is arranged, and with a push rod 8. By means of the push rod 8, the force of the compression spring is transmitted from the first bar 2 to the second bar 3 in such a way that a pivoting force is generated between the two bars 2, 3 both in the extension direction and in the flexion direction. It is therefore a stretching device acting at both ends. Since a spring force mechanism of this kind is already known, it is explained only insofar as is necessary for an understanding of the invention.

The orthesis illustrated permits simple and precise adjustment, without a tool, of the pivot range limits in the extension direction and flexion direction by means of two adjustment pins 9, 10, and also simple adjustment of a dead point starting from which the spring force mechanism acts in the flexion direction and extension direction, by turning a control knob 11.

The individual components of this orthesis are explained in detail below with reference to FIG. 2. The pivot axis is indicated there by 102. The core of the bar hinge 4, which connects the two bars 2, 3 to one another, is a housing 12 (shown in more detail in FIGS. 4A and 4B) which is fixedly screwed onto the first bar 2 in an edge area. Arranged on the front face of the housing 12 in FIG. 2 there are: an elastomer ring 13, a first click-stop dial 14 for adjusting the extension limit stop, a second click-stop dial 15 for adjusting the flexion limit stop, a locking disk 16 which surrounds the click-stop dials 14, 15, an elastomer ring 17, a rotation part 18 (shown in more detail in FIG. 5), and a cover plate 19.

Arranged on the rear face of the housing 12 in FIG. 2 there are: a central rotation block 20 for adjusting the dead point of the spring force mechanism, a catch 21 arranged axially displaceably in the rotation block 20, the second bar 3, onto which a limit stop device 22 is fixedly screwed, the first bar 2, and a retaining plate 23.

The spring housing 7 containing the compression spring 24 is fixedly screwed onto the second bar 3. The compression spring 24 bears with its front end on a pressure cylinder 25 which is connected in an articulated manner to the push rod 8. At the opposite end, the push rod 8 is connected in an articulated manner to a radially projecting arm 26 of the central rotation block 20. The thrust force of the compression spring 24 is thus transmitted constantly to the arm 26 by the push rod 8.

At the rear end, the compression spring 8 is supported on a spring-tensioning plug 27 which is designed as a spindle nut with internal thread. A spring-tensioning shaft 28, which represents a spindle, is screwed into this spring-tensioning plug 27. The spring-tensioning shaft 28 can be set in rotation via a crank 29, a crankshaft 30 and gear wheels 31, by which means the spring-tensioning plug 27 is moved in the axial direction, so that the pretensioning force of the compression spring 24 can be adjusted. The gear wheels 31 are mounted in a gear housing 32.

FIG. 2 also shows the details of the control knob 11 with which an eccentric part 33 can be turned. As will be explained in more detail later, the eccentric part 33 is used for locking and releasing a radially arranged blocking pin 34, which is mounted with possibility of longitudinal displacement in the arm 26 of the rotation block 20.

The individual parts and their functions will now be described in detail with reference to FIGS. 3 to 13.

The housing 12 is shown from the front in FIG. 4A and from the rear in FIG. 4B. The housing 12 has a plane middle wall 35 which is interrupted by a longitudinal slit 36 in the shape of an arc of a circle. The longitudinal slit 36 extends over about 180°. Extending upward and perpendicularly from the middle wall 35 there is a circumferential wall 38 which is interrupted by slits 37 distributed uniformly about the circumference and which thus forms individual fingers. The width of the slits 37 corresponds approximately to the width of the fingers. Moreover, protruding above the middle wall 35 there is a central sleeve portion 39 which serves as a rotation bearing for the click-stop dials 14, 15 shown in FIG. 8. Middle wall 35 and sleeve portion 39 have a central bore 40 running continuously through them.

As can be seen from FIG. 4B, a circumferential wall 41 extends above the rear face of the middle wall 35. The height of the circumferential wall 41 is higher in a first circumferential portion 42 than in a second circumferential portion 43. Situated in the first circumferential portion 42 there are several axially oriented threaded bores 44, allowing the first bar 2, which bears on the first circumferential portion 42, to be screwed tight by means of screws 45 (FIG. 3). The height of the second circumferential portion 43 is reduced compared to the first circumferential portion 42, along a circumferential length of about 200°, so as to create a corresponding free space for the first bar 2 and the push rod 8 which extend radially beyond the second circumferential portion 43. Provided in the second circumferential portion 43 there are also a plurality of radial blocking bores 46 which are spaced apart uniformly in the circumferential direction and into which the blocking pin 34 of the central rotation block 20 can be introduced, by which means the rotation position of the rotation block 20 relative to the housing 12 is blocked. The rotation position of the rotation block 20, and thus that of the coupling point 47 (FIG. 2) of the push rod 8 on the arm 26, can thus be adjusted by means of the rotation block 20, with the blocking pin 34 drawn back, first being turned to the desired rotation position, whereupon the blocking pin 34 is latched in the desired blocking bore 46. This procedure is described in more detail below.

As can be seen from FIG. 3, the first elastomer ring 13, closely surrounding the central sleeve portion 39, sits on the plane middle wall 35 of the housing 12. The first click-stop dial 14 sits on the first elastomer ring 13, followed by the second click-stop dial 15 and the elastomer ring 17.

These click-stop dials 14, 15 are of largely identical design, so that in FIG. 8 only one of these click-stop dials 14, 15 is shown. The click-stop dials 14, 15 are circular and have a central through-opening 49, so that they can be fitted with slight play onto the central sleeve portion 39 of the housing 12. The central sleeve portion 39 thus forms a rotation bearing for the click-stop dials 14, 15. Moreover, the click-stop dials 14, 15 can also move axially slightly, as far as is permitted by the elastomer rings 13, 17 between which they are clamped and which are made of relatively soft material.

On their outer circumference, the click-stop dials 14, 15 have a relatively fine outer toothing 50, which is shown diagrammatically in FIG. 8. Between the outer circumference and the through-opening 49, a continuous longitudinal slit 51 in the shape of an arc of a circle extends over an angle range of approximately 200°. The two click-stop dials 14, 15 are mounted in such a way that the two longitudinal slits 51 can at least for the most part be made congruent, and these in turn lie over the slit 36 of the housing 12. In this way, a limit stop pin 52 shown in FIG. 3, and which is connected fixedly to the second bar 3 via a base part 53 and screws 54, can extend upward through the longitudinal slits 36, 51 from below and move along these. Since the click-stop dials 14, 15 are blocked via the outer toothings 50 in a rotationally fixed manner relative to the housing 12 and thus relative to the first bar 2, the limit stop pin 52 can move inside the longitudinal slits 36, 51 until it has arrived at the end of the longitudinal slits 51 and either strikes against the limit stop 55 or against the opposite limit stop 56. It is thus evident that the position of the pivot range limits depends on the position of the limit stops 55, 56 relative to the housing 12 and, consequently, to the first bar 2, and that, by independent turning of the click-stop dials 14, 15 relative to the housing 12, the pivot range limits in the flexion direction and extension direction can be adjusted independently of one another.

In order to be able to rotate the click-stop dials 14, 15 to the desired rotation position after they have been unlocked (in a manner which is described in more detail below), each click-stop dial 14, 15 has, as can also be seen from FIG. 3, an adjustment pin 57, 58 which protrudes upward through a longitudinal slit 59 shaped as an arc of a circle in the cover plate 19 (FIG. 6) and projects slightly upward over the cover plate 19, so that the adjustment pins 57, 58 can be moved with the fingers. Along this longitudinal slit 59, a suitable scale 60 is set out on the cover plate 19 so as to make it possible to read off the position of the limit stops 55, 56 and thus the pivot range limits in the flexion direction and extension direction.

The click-stop dials 14, 15 are locked in the desired rotation position via the locking disk 16, which is shown in more detail in FIGS. 7A and 7B. The locking disk 16 is of annular design and has a clear internal diameter corresponding to the external diameter of the click-stop dials 14, 15. On the inner circumferential wall, the locking disk 16 has an inner toothing 61 which can be brought into engagement with the outer toothing 50 of the click-stop dials 14, 15. Moreover, the locking disk 16 has radial projections 62 which are distributed uniformly about its outer circumference and whose length (in the circumferential direction) corresponds to the width of the slits 37 in the circumferential wall 38 of the housing 12. When the locking disk 16 is fitted in the housing 12, the radial projections 62 extend through the slits 37 of the housing 12, so that the locking disk is received in the housing 12 in a manner fixed in terms of rotation, but axially displaceably. The external diameter of the radial projections 62 is also slightly greater than the external diameter of the circumferential wall 38 of the housing 12, so that the radial projections 62 extend radially outward slightly beyond the circumferential wall 38.

The locking disk 16 can be displaced axially relative to the housing 12 by means of the rotation part 18. For this purpose, the radial projections 62 have an external thread 63 which is in engagement with an internal thread 64 (FIG. 5) of the rotation part 18. The substantially sleeve-shaped rotation part 18 forms the radial outer jacket of the bar hinge 4 which covers the upper part of the housing 12, including the circumferential wall 41 in which the blocking bores 46 are located. The rotation part 18 is not axially displaceable, but is fitted rotatably on the housing 12. For this purpose, the rotation part 18 has, in its lower third, a radially inwardly projecting shoulder 65 which rests on an edge projection 66 of the housing 12 (FIG. 3) and fixes the rotation part 18 axially toward the bottom. An axial displacement of the rotation part 18 toward the top is prevented by a radially inwardly projecting shoulder 67 which is located at the upper end of the rotation part 18 and over which the edge of the cover plate 19 engages.

As can also be seen from FIG. 3, an axial free space 68 is present between the plane middle wall 35 and the first click-stop dial 14, because of the elastomer ring 13 lying between them. In the same way, an axial free space 69 is present between the second click-stop dial 15 and the cover plate 19, because of the elastomer ring 17 lying between them. The height of the free spaces 68, 69 is slightly greater than the thickness of the click-stop dial 14, 15. Because they have the same height, the elastomer rings 13, 17 hold the click-stop dials 14, 15, when viewed in the axial direction, in the center between the middle wall 35 and the cover plate 19.

The locking disk 16 forms, together with the rotation part 18, a fixing device for releasing and for blocking the click-stop dials 14, 15.

The locking disk 16, which has the same thickness as the two click-stop dials 14, 15 taken together, can be moved up or down in the manner of a spindle by turning the rotation part 18, as is shown in FIGS. 12A to 12C. In FIG. 12A, the locking disk 16 is situated at the same height as the two click-stop dials 14, 15. Both click-stop dials 14, 15 are therefore in engagement with the inner toothing 61 of the locking disk 16 and a blocked by the latter in terms of rotation. When the rotation part 18 is turned in a defined direction, the locking disk 16 can be displaced upward until the lower click-stop dial 14 is disengaged from the locking disk 16. This state is shown in FIG. 12B. The lower click-stop dial 14 can therefore be brought by hand to the desired rotation position by means of the adjustment pin 57, for example in order to adjust the extension limit stop. If the rotation ring 18 is then turned in the opposite direction, the locking disk 16 can be moved downward until the upper click-stop dial 15 is disengaged from the locking disk 16. This state is shown in FIG. 12C. The upper click-stop dial 15 can now be turned to the desired position by means of the adjustment pin 58, for example in order to adjust the flexion limit stop. When both click-stop dials 14, 15 have been correctly adjusted, the rotation part 18 is screwed back again until the locking disk 16 locks both click-stop dials 14, 15 (FIG. 12A).

Since, upon axial movement of the locking disk 16 from the position shown in FIG. 12B or 12C to the middle position shown in FIG. 12A, it can happen that the inner toothing 61 of the locking disk 16 does not mesh properly with the outer toothing 50 of the click-stop dials 14, 15, and instead thread teeth strike against thread teeth, the elastomer rings 13, 17 are made relatively soft and permit yielding of the click-stop dials 14, 15 in the axial direction. In this way, mutual engagement of the toothings is made easier.

The cover plate 19 is shown in FIG. 6. As can be seen, the top face bears the indications "Flexion adjustment", "Stop" and "Extension adjustment". These indications show in which direction the rotation part 18 has to be turned in order to free the click-stop dial for the flexion limit stop or the click-stop dial for the extension limit stop. In the "Stop" position, both click-stop dials 14, 15 are locked.

Referring to FIGS. 9 to 11, the dead-point adjustment mechanism is now described in more detail, with which mechanism it is possible to adjust the dead point starting from which the direction of action of the spring force mechanism is reversed from flexion to extension, or vice versa. For this purpose, the central rotation block 20, which is shown in detail in FIG. 11, has a cylindrical portion 70 which is fitted into the central bore 40 of the housing 12 and is mounted so as to be able to rotate therein. Adjoining the cylindrical portion 70 there is a cylindrical portion 72 of greater diameter, on which the arm 26 is integrally formed in such a way that it extends radially away from the portion 72. A circumferential radial projection 73 adjoins the cylindrical portion 72. This radial projection 73 serves as a bearing surface for the circular end portion 74 of the second bar 3. Adjoining the radial projection 73 there is a cylindrical portion 75 (FIG. 11) which serves as a radial bearing for the second bar 3. Axial threaded bores 76 are provided in the cylindrical portion 75 in order to be able to screw tight the retaining plate 23 by means of screws 77 indicated in FIG. 3.

As can be seen from FIGS. 9 and 10, a central axial bore 78 is located in the cylindrical portion 70 of the rotation block 20, in which a cylindrical portion 79 of the eccentric part 33 is rotatably mounted. The bore 78 opens into a circular pocket 80 of greater diameter which is arranged eccentrically with respect to the bore 78. The pocket 80 is used to receive an eccentric cylinder portion 81 of the eccentric part 33, so that the latter cannot turn when the eccentric cylinder portion 81 lies in the pocket 80. This position is shown in FIG. 10.

The pocket 80 is adjoined by an axial, central bore 82 of greater diameter. The diameter of this bore 82 is such that the eccentric part 33 can be turned in any desired way when it has been displaced upward from the position shown in FIG. 10 in the axial direction, i.e. in the direction of the arrow 91, and so far that the eccentric cylinder portion 81 is situated above the pocket 80.

Directly above the pocket 80, as can be seen from FIG. 9, a radial bore 83 extends through the whole arm 26 and is used for receiving the blocking pin 34 and a compression spring 84 (FIG. 10). In an outer end portion 85, the bore 83 has a smaller diameter, so that a shoulder 86 is formed on which the outer end of the compression spring 84 is supported. The blocking pin 34 has a shaft 87 and a head 88 of greater diameter on which the opposite end of the compression spring 84 is supported. The length of the blocking pin 34 is also such that its outer end protrudes beyond the arm 26 and into one of the blocking bores 46 when the opposite end of the head 88 is flush with the wall of the bore 82. When, in this state which is shown in FIG. 10, the eccentric cylinder portion 81 of the eccentric part 33 is situated inside the pocket 80, the blocking pin 34 cannot move back into the bore 82, because it strikes against the eccentric cylinder portion 81. The blocking pin 34 is thus locked in a manner preventing a rotation movement of the rotation block 20 relative to the housing 12. The coupling point 47 (FIG. 2), which is formed by an axial bore 89 in the arm 26 (FIG. 10) and by a hinge pin 90 (FIG. 3) fastened in the push rod 8 and engaging in the bore 89, is thus fixed relative to the housing 12.

In order to adjust the coupling point 47 and thus the dead point of the spring force mechanism, the eccentric part 33 is displaced in the direction of the arrow 91 (FIG. 10) counter to the force of a compression spring 92 (FIG. 3) by means of turning the control knob 11 until the eccentric cylinder portion (81) lies outside the pocket 80. The eccentric part 33 can then be turned through 180° by means of the control knob 11, which is connected to the eccentric part 33 in a rotationally fixed manner via a square part 93, as a result of which the blocking pin 34 moves back into the bore 82 under the force of the compression spring 84, and the opposite end of the blocking pin 34 can emerge from the blocking bore 36. The rotation block 20 can now be rotated farther to another desired blocking bore 46, whereupon the blocking pin 34 is brought back into the locking engagement position by means of turning the eccentric part 33 back.

With the blocking pin 33 unlocked, the rotation block 20 is rotated to the desired position relative to the housing 12 by means of the second bar 3, which can be connected in a rotationally fixed manner to the rotation block 20 via the catch 21 shown in FIGS. 2 and 3. The catch 21 has a hub-shaped middle part 94, from which two wings 95 extend in opposite directions.

In normal operation of the orthesis, i.e. when the eccentric part 33 in FIG. 10 is at the lowest position shown, the hub-shaped middle part 94 of the catch 21 is arranged at the lowest possible position inside the bore 82, the wings 95 lying deep in radial grooves 96 of the central rotation block 20 (FIG. 11). In this state, the wings 95 do not extend upward past the radial projection 73, so that the second bar 3 can turn about the cylindrical portion 75 of the rotation block 20. However, if the eccentric part 33 is pushed upward in order to unlock the blocking pin 34 (see arrow 91 in FIG. 10), the catch 21 is thus also pushed upward, as a result of which the wings 95 can be pushed axially into the area of the cylindrical portion 75 and into lateral grooves 97 (FIG. 13) which extend radially outward from the central bearing bore 98 of the second bar 3. In this way, the second bar 3 is connected in a rotationally fixed manner to the rotation block 20, so that the latter can be turned in the desired manner by means of the second bar 3 when the blocking pin 34 is unlocked.

As can be seen from FIG. 3, the hub-shaped middle part 94 of the catch 21 serves to support the compression spring 92. The opposite end of the compression spring 92 is supported on the outer, central retaining plate 23. If the eccentric part 33 is turned in such a way that the eccentric cylinder portion 81 can move back into the pocket 80 of the rotation block 20, the compression spring 92 presses the catch 21 together with the eccentric part 33 back into the position shown in FIG. 3. In this way, the wings 95 of the catch 21 disengage from the lateral grooves 97 of the second bar 3, so that the latter can be pivoted again within the set pivot range limits about the rotation block 20 and thus relative to the first bar 2.

To minimize the friction between the circular end part of the first bar 2 and the circular end part of the second bar 3, a shim element 99 is inserted between these end parts, as can be seen from FIG. 3.

In the illustrative embodiment shown, the internal thread 64 of the rotation part 18 (FIG. 5) is arranged, for production engineering reasons, on a separate thread ring 100 which is connected by means of a suitable adhesive to a jacket 101 of the rotation part 18. Alternatively, however, it is also entirely possible to form the internal thread 64 directly on the jacket 101.

The invention has been described taking the example of an elbow orthesis, but it can be used for other ortheses too, for example knee ortheses.

The invention claimed is:

1. An orthesis with
   a first bar which can be fastened to a first body part,
   a second bar which can be fastened to a second body part,
   a bar hinge for pivotable connection of said first and second bars,
   at least one click-stop dial which is rotatable about a pivot axis, can be blocked in different rotation positions and is used for adjusting a pivot range limit, and a fixing device for blocking said at least one click-stop dial, characterized in that said fixing device has a locking disk which is displaceable in the direction of said pivot axis, is mounted in a rotationally fixed manner in relation to said first bar and can be moved, by being displaced between a blocking position, in which said locking disk engages radially over said at least one click-stop dial and is in locked form-fit engagement with said at least one click-stop dial, and a release position, in which said locking disk is disengaged from said at least one click-stop dial.

2. The orthesis as claimed in claim 1, characterized in that said at least one click-stop dial has an outer toothing, and said locking disk has an inner toothing which can be moved into and out of meshing engagement with said outer toothing of said at least one click-stop dial.

3. The orthesis as claimed in claim 1, characterized in that said locking disk has a thread and can be moved in the manner of a spindle via said thread.

4. The orthesis as claimed in claim 1, characterized in that said locking disk has a thread on its radial outer circumferential surface, and in that said fixing device has an axially fixed rotation part which radially surrounds said locking disk and has an internal thread, which rotation part engages with said thread said of said locking disk and, when rotated, causes an axial displacement of said locking disk.

5. The orthesis as claimed in claim 1, characterized in that two said click-stop dials are provided for adjusting said pivot range limits in the extension direction and flexion direction, said click-stop dials being arranged parallel and next to one another and being able to be blocked simultaneously by the same said locking disk.

6. The orthesis as claimed in claim 5, characterized in that said fixing device is designed in such a way that, by displacing said locking disk in one direction, said extension click stop dial is released, and, by displacing said locking disk in the opposite direction, said flexion click-stop dial is released.

7. The orthesis as claimed in claim 1, characterized in that said bar hinge has a housing fixedly connected to said first bar and with a circumferential wall partially surrounding said locking disk, in that said locking disk has radial projections, and in that peripheral wall is provided with slits through which said radial projections are guided in order to prevent rotation of said locking disk.

8. The orthesis as claimed in claim 7, characterized in that said housing has a central sleeve portion designed as a rotation bearing for said at least one click-stop dial, in that a spring force mechanism is provided in order to pretension said second bar relative to said first bar both in the extension direction and in the flexion direction, and in that a dead-point adjustment device for said spring force mechanism is mounted rotatably inside said sleeve portion.

9. The orthesis as claimed in claim 8, characterized in that said dead-point adjustment mechanism comprises a rotation block in which a blocking pin is displaceably guided transversely with respect to said pivot axis, in that said housing has a plurality of radial blocking bores which are spaced apart in the circumferential direction of said housing, and in that an eccentric part is mounted rotatably inside said rotation block in order to keep said blocking pin in engagement with a blocking bore or to permit removal of said blocking pin from said blocking bore.

10. The orthesis as claimed in claim 9, characterized in that said rotation block of said dead-point adjustment mechanism is designed as a rotation bearing for said second bar.

\* \* \* \* \*